US008147450B2

(12) United States Patent
Yang (10) Patent No.: US 8,147,450 B2
(45) Date of Patent: Apr. 3, 2012

(54) DISPOSABLE SELF-DESTRUCTION SAFETY SYRINGE WITHOUT FLUID RESIDUA

(75) Inventor: Yuhe Yang, Shantou (CN)

(73) Assignee: Shantou Wealy Medical Instrument Co., Ltd, Shantou, Guangdong Province (CN)

( * ) Notice: Subject to any disclaimer, the term of this patent is extended or adjusted under 35 U.S.C. 154(b) by 0 days.

(21) Appl. No.: 12/990,998

(22) PCT Filed: May 6, 2009

(86) PCT No.: PCT/CN2009/071657

§ 371 (c)(1),
(2), (4) Date: Nov. 4, 2010

(87) PCT Pub. No.: WO2009/135439
PCT Pub. Date: Nov. 12, 2009

(65) Prior Publication Data
US 2011/0060278 A1  Mar. 10, 2011

(30) Foreign Application Priority Data

May 8, 2008  (CN) .......................... 2008 1 0096785
Apr. 13, 2009  (CN) ..................... 2009 2 0150008 U (51) Int. Cl.
*A61M 5/00* (2006.01)
(52) U.S. Cl. ..................................................... 604/110
(58) Field of Classification Search ................... 604/110
See application file for complete search history.

(56) References Cited

U.S. PATENT DOCUMENTS

| 5,374,250 | A | * | 12/1994 | Dixon | 604/110 |
| 5,578,011 | A | * | 11/1996 | Shaw | 604/110 |
| 5,800,403 | A | * | 9/1998 | Pressly et al. | 604/195 |
| 6,015,438 | A | * | 1/2000 | Shaw | 604/195 |
| 7,267,664 | B2 | * | 9/2007 | Rizzo | 604/110 |
| 2001/0053886 | A1 | * | 12/2001 | Caizza | 604/110 |
| 2003/0050601 | A1 | * | 3/2003 | Righi et al. | 604/110 |
| 2004/0054324 | A1 | * | 3/2004 | Montalvo et al. | 604/110 |
| 2004/0116857 | A1 | | 6/2004 | Kiehne | |
| 2005/0096604 | A1 | | 5/2005 | Maggioni | |
| 2006/0111669 | A1 | * | 5/2006 | Kuan | 604/110 |
| 2008/0140005 | A1 | * | 6/2008 | Luo et al. | 604/110 |
| 2009/0093760 | A1 | * | 4/2009 | Kiehne | 604/110 |
| 2011/0092902 | A1 | * | 4/2011 | Kiehne | 604/110 |

FOREIGN PATENT DOCUMENTS

| CN | 1252311 A | 5/2000 |
| CN | 2778297 Y | 5/2006 |
| WO | 2006119570 A1 | 11/2006 |

* cited by examiner

*Primary Examiner* — Nicholas Lucchesi
*Assistant Examiner* — Victoria P Campbell
(74) *Attorney, Agent, or Firm* — Hultquist, PLLC; Kelly K. Reynolds; Steven J. Hultquist (57) ABSTRACT

A disposable self-destruction safety syringe without fluid residua comprises a syringe tube (1), a push rod (2), a needle mount (3) and a needle (4). The push rod (2) and the needle mount (3) are mounted in the syringe tube (1). A plunger (5) slidably fitting with the inside wall of the syringe tube (1) is provided on the front end of the push rod (2). Wherein, an automatic retraction means (6) is mounted in the front end of the chamber of the push rod (2). The automatic retraction means (6) and the needle mount (3) are each provided with a snap-latch member, respectively, for connecting the needle mount (3) with the automatic retraction means (6). Each of said snap-latch member is provided with a fluid pass channel, such that the fluid remaining inside the syringe tube (1) flows, through the fluid pass channel when the snap-latch members form an interference fit and engage with each other, into the chamber of the needle mount (3) and the needle (4).

12 Claims, 8 Drawing Sheets

DISPOSABLE SELF-DESTRUCTION SAFETY SYRINGE WITHOUT FLUID RESIDUA

CROSS-REFERENCE TO RELATED APPLICATIONS

This application is a U.S. national phase application under the provisions of 35 U.S.C. §371 of International Patent Application No. PCT/CN09/71657 filed May 6, 2009, which in turn claims priority of Chinese Patent Application No. 200810096785.1 filed May 8, 2008 and Chinese Patent Application No. 200920150008.0 filed Apr. 13, 2009. The disclosures of such international patent application and Chinese priority patent applications are hereby incorporated herein by reference in their respective entireties, for all purposes.

FIELD OF THE INVENTION

The present invention relates to a self-destruction safety syringe, in particular, to a disposable self-destruction safety syringe without fluid residua.

BACKGROUND OF THE INVENTION

Syringe is one of the most common medical devices. In order to reduce the spread of the blood-borne diseases among the patients, all the countries in the world make law to compulsorily popularize and use disposable syringe. However, current common disposable syringes have defects in that such syringes are often repeatedly used, such syringes are provided without safety means, and the needles thereof are exposed out after injection. Therefore, on one hand the disposable syringes are easily used by the lawbreakers or drug addicts; and on the other hand the syringes supposed to be disposable are often reused, which easily causes the virus spread or raises cross infection. In order to prevent the occurrence that the disposable syringes are re-purchased, re-sold and reused and to avoid the infection of the medical care personnel who may be stuck by the needles when recycling the syringes, all the countries in the world are under the research of self-destruction safety syringe.

Self-destruction safety syringes currently known are mainly plunger piercing type or manual pull-type with syringe needle, and further there is also another type that the needle mount is provided with an automatic spring, in which after the fluid has been injected, the push rod is pushed to the frontmost end of the syringe tube and meantime the needle mount is retracted into the syringe tube together with the syringe needle so as to prevent the syringe needle from protruding out to stick someone. However, all these self-destruction safety syringes still have various defects in their designs.

Chinese Patent CN200980874Y discloses a safety self-destruction syringe, in which the needle mount and the syringe needle can automatically retract into the push tube by providing an automatic retraction means in the push tube. However, this invention neither thoroughly solves the problem of how to compress the compression spring into the lower part of the push tube before use (the inside wall of the push tube is smooth without any object for hooking and thus the compression spring cannot be compressively hooked) nor solves the problem that how the residual fluid can pass through and flow into the needle during injection.

U.S. Pat. No. 5,211,628 discloses a syringe with an automatic retracting means. This syringe adopts a biasing member of spring around the shank portion of the connecting shaft, the spring has an upper end engaged with the top terminal wall of the push rod and a lower end embedded and locked in the brake groove by the biasing member. In addition, an actuating section has a pushing terminal moving together with the puncturing end of the connecting shaft. When the coupling end of the connecting shaft disengages from the outer adjacent area under pressure, the pushing terminal on the spring will move downwardly together with the puncturing end, the pulling terminal can pull the lower end of the spring out of the brake groove. Furthermore, a gasket is placed to bring the bulge ring to the rear chamber of the outer cover to engage with the front wall of the rear chamber so as to provide a resistance for the formation of the gasket. This resistance supports for positioning of the bulge ring so as to prevent the movement of a certain position of the front wall of the back chamber of the gasket in hypodermic or intravenous injection puncture, thereby the bulge ring being allowed to disengage from a certain portion of the back chamber of the syringe, therefore, when the first external force is exerted, the tubular needle gauge can move with the bulge ring in the inside wall of the outer cover. However, this syringe still has some defects: when the smallest part of the snap-latch means and the biggest part of the needle mount form an interference fit with each other, the residual fluid is sealed and cannot circulate, at this moment, if the push rod is pushed forward with a large pressure, the needle punctured subcutaneously will be vibrated and causes pain to the patient injected.

Chinese Patent No. 2817873Y also discloses a self-destruction safety syringe. This syringe uses a spring-back device of a steel needle which is arranged in the outer needle mount to form a needle head assembly connected with the top end of the injection cylinder through threads. This syringe not only has the characteristic of the ordinary disposable syringe with the spring-back steel needle, but also the producing process thereof becomes simple and the assembly is convenient. However, it still cannot solve the problem of the resistance of the end plug, and the spheroidal design of the front end of the end plug also will increase the amount of the residual fluid.

U.S. Pat. No. 6,379,336 provides a self-destruction safety syringe with an improved structure, however, the structure of the syringe is quite complex and not easy to be assembled. And moreover, the cost is high and the volume of the fluid residual is high, which is unacceptable especially in the case that the injection fluid is expensive.

Although a lot of self-destruction safety syringes have been developed, those syringes have various structural defects, especially lots of residual fluid is sealed when the connection structures form an interference fit with each other. The present invention is aimed to make a further improvement to the structure of the existing self-destruction safety syringes so as to effectively solve the above technical problems.

SUMMARY OF THE INVENTION

The object of the present invention is to provide a disposable self-destruction safety syringe without fluid residua, in which, the needle mount together with the needle can safely and automatically retract into the syringe tube after injection with no fluid residua left in the syringe tube.

The object of the present invention is achieved by the following technical solutions: a disposable self-destruction safety syringe without fluid residua, comprising a syringe tube, a push rod, a needle mount and a needle, wherein the needle is mounted on the needle mount, the needle mount and the push rod are mounted in the syringe tube, and a plunger slidably fitting with the inside wall of the syringe tube is further provided on the front end of the push rod, and wherein an automatic retraction means is mounted in the front end of the chamber of the push rod, the automatic retraction means comprises a retraction rod, a compression spring fitted around the retraction rod, an elastic rubber washer mounted on the terminal end of the retraction rod and a position-limiting ring provided on the inside wall of the push rod. The elastic rubber washer and the position-limiting ring form an interference fit with each other so as to secure the automatic retraction means in the front end of the chamber of the push rod. The retraction rod of the automatic retraction means and the needle mount are each provided with a respective snap-latch member, and the two snap-latch members form an interference fit with each other for connecting the needle mount with the automatic retraction means. Each of the snap-latch member is provided with a fluid pass channel such that the fluid remaining inside the syringe tube flows through the fluid pass channel, when the snap-latch members engage with each other to form interference fit, into the chamber of the needle mount and the needle.

A fluid-tight ring is further provided between the automatic retraction means and the front end of the chamber of the push rod for sealing the gap between the automatic retraction means and the chamber of the push rod to prevent fluid leakage.

As an optional solution, the needle mount is provided with a first step, a second step and a third step, in which the first step and the tube hole on the top end of the syringe tube fit with each other to prevent the needle from inclining during injection, a hook step is provided between the second step and the third step to prevent the needle mount from retracting when a force is exerted on the needle mount during injection, and the snap-latch member is provided on the third step. As an optional solution, a ledge is provided on the inside wall of the needle mount for limiting the position of the needle when being mounted.

The syringe tube is provided inside with a fluid-tight ring fitted on the needle mount for securing the needle mount and for sealing the gap between the needle mount and the inside wall of the syringe tube to prevent fluid leakage. A chamber is formed between the front surface of the fluid-tight ring and the inside wall of the syringe tube for accommodating the fluid-tight ring when the fluid-tight ring slides forward and disengages from the needle mount.

As an optional solution, an annular push block is provided on the circumference of the top end of the push rod for pushing the fluid-tight ring in the syringe tube to slide forward so as to disengage from the needle mount. The annular push block is provided with a fluid pass channel such that fluid remaining inside the syringe tube flows through the fluid passage, when the annular push block pushes the fluid-tight ring to slide forward to disengaged from the needle mount, into the chamber of the needle mount and the needle.

A convex retaining ring is further provided on the inside wall of the syringe tube at the rear end of the fluid-tight ring for preventing the needle mount from retracting when a force is exerted on the needle mount during injection. This convex retaining ring forms a double resistance together with the hook-step provided between the second and third steps of the needle mount for effectively preventing the needle mount from retracting when a force is exerted on the needle mount during injection.

Each of the plunger, the elastic rubber washer and the fluid-tight rings is made of the synthetic rubber materials.

The self-destruction safety syringe according to the present invention further comprises a needle cannula on the front end of the syringe tube and a push plug provided at the terminal end of the push rod.

The self-destruction safety syringe according to the present invention makes improvements on the structure. By the action of the interference fit between the elastic rubber washer and the position-limiting ring, the automatic retraction means is securely located on the front end of the chamber of the push rod, and when the injection is finished, the elastic rubber ring is disengaged from the position-limiting ring by a counter-force, and the retraction rod together with the needle mount and the needle is pushed and retracted into the syringe tube under the action of the elastic force of the spring so as to realize safe disposable use with the automatic self-destruction. Moreover, by providing the fluid pass channels on the snap-latch members of the automatic retraction means and the needle mount, the fluid remaining inside the syringe tube can flow into the chamber of the needle mount and the needle when the automatic retraction means and the needle mount engage with each other to form an interference fit and thus be injected into the human body. Therefore, no fluid residua is left inside the syringe tube. Further, a structure with double resistance is formed by providing the hook-step on the needle mount and providing the convex retaining ring on the inside wall of the syringe tube, thus of the retraction of the needle mount may be effectively prevented when a force is exerted on the needle mount during injection. Further, by providing the first step slidably fitting with the tube hole on the top end of the syringe tube on the needle mount, the incline of the needle during injection can be prevented.

DETAILED DESCRIPTION OF EMBODIMENTS

The First Embodiment

As shown in FIG. 1 to FIG. 4, the self-destruction safety syringe according to the present invention comprises a syringe tube 1, a push rod 2, a needle mount 3, a needle 4, a needle cannula 11, a handle 12 and a push plug 13, wherein the needle 4 is mounted on the needle mount 3, the needle mount 3 and the push rod 2 are mounted in the syringe tube 1, and a plunger 5 slidably fitting with the inside wall of the syringe tube 1 is further provided on the front end of the push rod 2.

Figure 1:
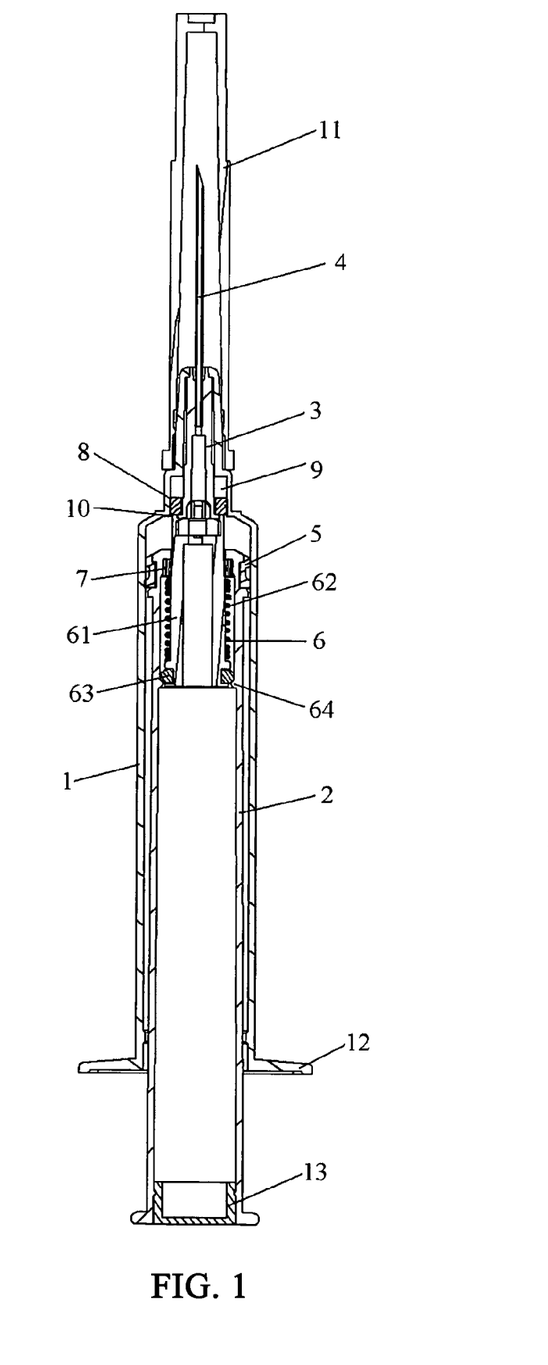
FIG. 1 is a structural scheme of the syringe of a first embodiment of the present invention.
Figure 4:
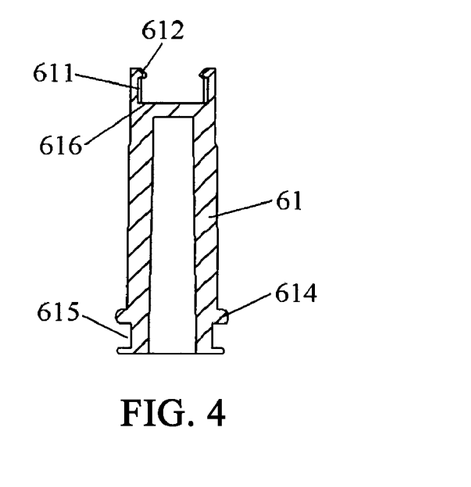
FIG. 4 is a structural scheme of the retraction rod of the first embodiment of the present invention.
Figure 4A:
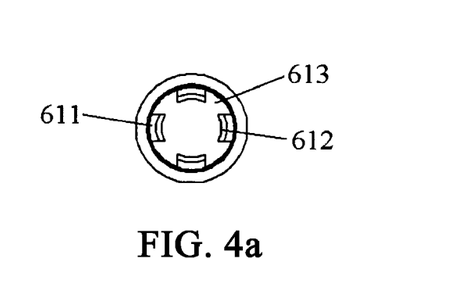
FIG. 4a is a top view of FIG. 4.

An automatic retraction means 6 is mounted in the front end of the chamber of the push rod 2. The automatic retraction means 6 comprises a retraction rod 61, a compression spring 62, an elastic rubber washer 63 and a position-limiting ring 64. A fluid-tight ring 7 is further provided between the front end of the automatic retraction means 6 and the front end of the chamber of the push rod 2. The front end of the automatic retraction means 6 is tightly pressed against the fluid-tight ring 7 so as to seal the gap between the automatic retraction means 6 and the chamber of the push rod 2 to prevent fluid leakage. Four annular sector-shaped push blocks 611 with equidistant intervals are provided on the circumference of the top end of the retraction rod 61. On the top end of each annular sector-shaped top blockpush push block 611 is further provided with an inner shackle 612. Fluid pass channels 613 are formed among the annular sector-shaped push blocks 611. The terminal end of the retraction rod 61 is provided with a ledge 614, a groove 615 is formed in the middle of the ledge 614, and an elastic rubber washer 63 is placed in the groove 615. A compression spring 62 is fitted around the retraction rod 61 with the front end thereof biased against the terminal end of the fluid-tight ring 7 and the rear end thereof biased against the front surface of the ledge 614 of the retraction rod 61. A position-limiting ring 64 is provided on the inside wall of the push rod 2 to form an interference fit with the elastic rubber washer 63 so as to securely locate the automatic retraction means 6 in the front end of the chamber of the push rod 2.

Figure 3:
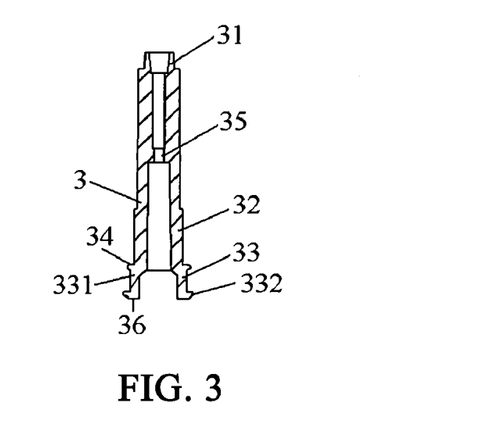
FIG. 3 is a structural scheme of the needle mount of the first embodiment of the present invention.
Figure 3A:
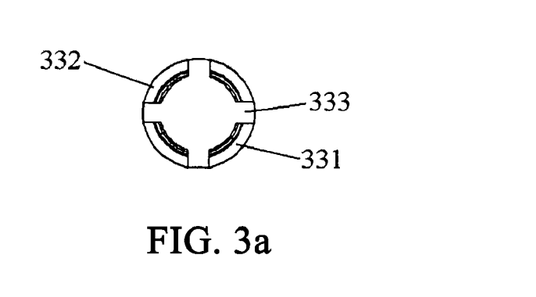
FIG. 3a is a bottom view of FIG. 3.

The needle mount 3 is provided with a first step 31, a second step 32 and a third step 33. The first step 31 slidably fits with the tube hole 14 in the center of the top end of the syringe tube 1 so as to prevent the needle from inclining during injection. A hook step 34 is provided between the second step 32 and the third step 33 to prevent the needle mount from retraction when a force is exerted on the needle mount during injection. The third step 33 is formed by four annular sector-shaped push blocks 331 with equidistant intervals. The top end of each annular sector-shaped push block 331 is further provided with an outer shackle 332. Fluid pass channels 333 are formed among the annular sector-shaped push blocks 331. The annular sector-shaped push blocks 331 of the needle mount 3 and the annular sector-shaped push blocks 611 of the automatic retraction means 6 are arranged corresponding to each other, and the outer shackles 332 on the annular sector-shaped push blocks 331 and the inner shackles 612 on the annular sector-shaped push blocks 611 may form an interference fit with each other when snap-latched. When the inner shackles 612 and the outer shackles 332 are snap-latched to each other, the needle mount 3 and the automatic retraction means 6 is connected to each other. Moreover, a ledge 35 is provided on the inside wall of the needle mount 3 for limiting the position of the needle 4 when being mounting.

The syringe tube 1 is equipped with a fluid-tight ring 8 fitted on the third step 33 of the needle mount 3 for securing the needle mount 3 and for sealing the gap between the needle mount 3 and the inside wall of the syringe tube 1 so as to prevent fluid leakage. The fluid-tight ring 8 has a same height as that of the third step 33 and has its front end tangent to the hook step 34 provided between the second step 32 and the third step 33 of the needle mount 3 so as to strengthen the securing of the needle mount 3. A chamber 9 is formed between the front surface of the fluid-tight ring 8 and the inside wall of the syringe tube 1, thus the fluid-tight ring 8 may be accommodated inside the chamber 9 when slide forward and disengage from the needle mount 3. In addition, on the inside wall of the syringe tube 1, a convex retaining ring 10 is further provided at the rear end of the fluid-tight ring 8 for securing the location of the fluid-tight ring 8 and preventing the needle mount from retracting when a force is exerted on the needle mount during injection. The convex retaining ring 10 and the hook step 34 provided between the second step 32 and the third step 33 of the needle mount 3 cooperate to form a double resistance for effectively preventing the needle mount from retracting when a force is exerted on the needle mount during injection.

Figure 2:
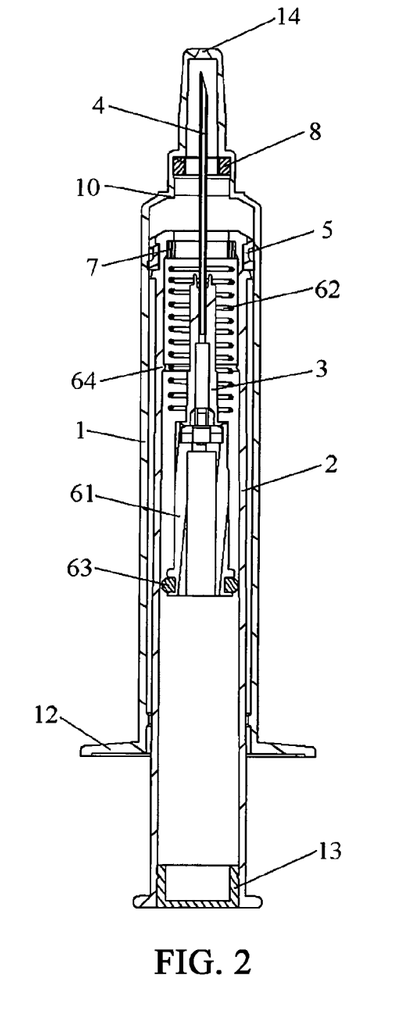
FIG. 2 is a structural scheme of the syringe of the first embodiment of the present invention in which the needle mount and the needle retract into the syringe tube.

During injection, as the push rod 2 is pushed forward, the fluid in the syringe tube 1 flows into the needle 4 through the chamber of the needle mount 3 and is injected into the human body or animal body through the needle 4. When the push rod 2 is pushed to the front end of the syringe tube 1 and the annular sector-shaped push blocks 611 on the automatic retraction means 6 are coupled to the annular sector-shaped push blocks 331 on the needle mount 3, the inner shackles 612 on the annular sector-shaped push blocks 611 and the outer shackles 332 on the annular sector-shaped push blocks 331 are snap-latched to each other under the action of thrust so as to connect the needle mount 3 with the automatic retraction means 6. Meanwhile, the annular sector-shaped push blocks 611 are coupled to the rear surface of the fluid-tight ring 8, so that the fluid-tight ring 8 is then pushed forward to slide forward and disengage from the third step 33 of the needle mount 3 and to enter the chamber 9. In the present embodiment, since the snap-latch member is formed by four annular sector-shaped push blocks arranged with equidistant intervals and having shackles, the resistance during the snap-latch is then quartered, and there will be almost no resistance sensed when the push rod is pushed for snap-latch. Moreover, since the fluid pass channels are formed among the annular sector-shaped push blocks, the fluid remaining in the syringe tube can flow through the fluid pass channels, when the automatic retraction means is coupled to and engaged with the needle mount, into the chamber of the needle mount 3 and into the needle 4, and therefore, there is no fluid residua in the syringe tube. After the inner shackles 612 and the outer shackles 332 are snap-latched to each other, the push rod 2 is further pushed so that the front end top surface 616 of the retraction rod 61 presses on the terminal end top surface 36 of the needle mount 3, and at this moment, the terminal end top surface 36 of the needle mount 3 will exert a counterforce against the front end top surface 616 of the retraction rod 61 forcing the elastic rubber washer 63 of the automatic retraction means 6 to disengage from the position-limiting ring 64, and then the compression spring 62 releases an elastic force to push the retraction rod 61 to retract together with the needle mount 3 and the needle 4 into the syringe tube 1.

The Second embodiment

As shown in FIG. 5 to FIG. 9, the self-destruction safety syringe according to the present invention comprises a syringe tube 1, a push rod 2, a needle mount 3, a needle 4, a needle cannula 11, a handle 12 and a push plug 13, wherein the needle 4 is mounted on the needle mount 3, the needle mount 3 and the push rod 2 are mounted in the syringe tube 1, and a plunger 5 slidably fitting with the inside wall of the syringe tube 1 is further provided on the front end of the push rod 2.

An automatic retraction means 6 is mounted in the front end of the chamber of the push rod 2. The automatic retraction means 6 comprises a retraction rod 61, a compression spring 62, an elastic rubber washer 63 and a position-limiting ring 64. A fluid-tight ring 7 is further provided between the front end of the automatic retraction means 6 and the front end of the chamber of the push rod 2. The front end of the automatic retraction means 6 is tightly pressed against the fluid-tight ring 7 so as to seal the gap between the automatic retraction means 6 and the chamber of the push rod 2 to prevent fluid leakage. Four spheroidal push blocks 617 arranged with equidistant intervals are provided on the top center of the retraction rod 61. The center of the throat of each spheroidal push block 617 is further provided with an outer shackle 612'. Fluid pass channels 613' are formed among the spheroidal push blocks 617. On the terminal end of the retraction rod 61 is provided with a ledge 614, a groove 615 is formed in the middle of the ledge 614, and an elastic rubber washer 63 is placed in the groove 615. A compression spring 62 is fitted around the retraction rod 61 with the front end thereof biased against the terminal end of the fluid-tight ring 7 and the rear end thereof biased against the front surface of the ledge 614 of the retraction rod 61. A position-limiting ring 64 is provided on the inside wall of the push rod 2 to form an interference fit with the elastic rubber washer 63 so as to securely locate the automatic retraction means 6 in the front end of the chamber of the push rod 2. In addition, on the circumference of the top end of the push rod 2, four annular sector-shaped push blocks 21 arranged with equidistant intervals are provided, and fluid pass channels 22 are formed among the annular sector-shaped push blocks 21.

Figure 7:
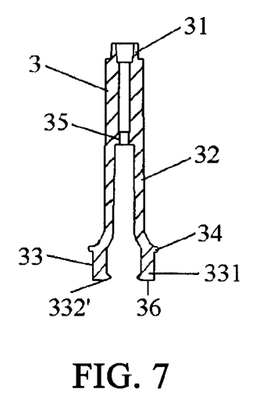
FIG. 7 is a structural scheme of the needle mount of the second embodiment of the present invention.
Figure 7A:
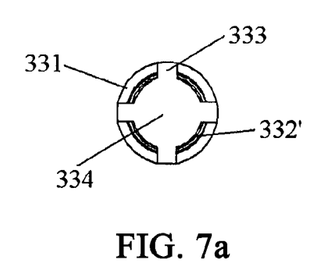
FIG. 7a is a bottom view of FIG. 7.
Figure 8:
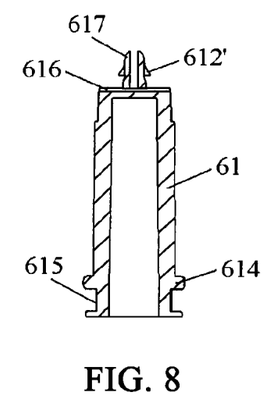
FIG. 8 is a structural scheme of the retraction rod of the second embodiment.
Figure 8A:
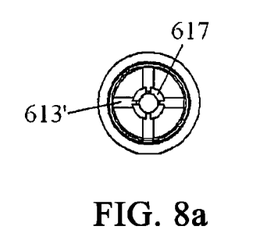
FIG. 8a is a top view of FIG. 8.
Figure 9:
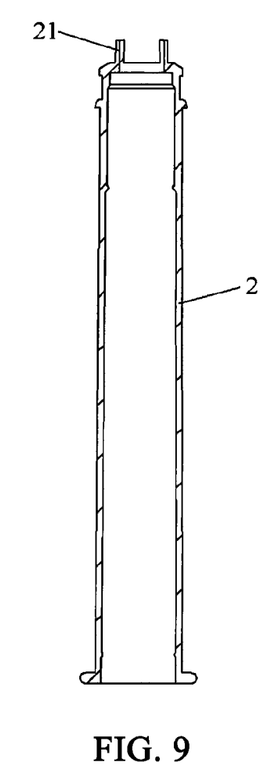
FIG. 9 is a structural scheme of the push rod of the second embodiment of the present invention.
Figure 9A:
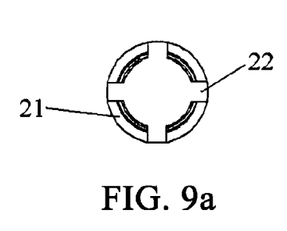
FIG. 9a is a top view of FIG. 9.

The needle mount 3 is provided with a first step 31, a second step 32 and a third step 33. The first step 31 slidably fits with the tube hole 14 in the center of the top end of the syringe tube 1 for preventing the needle from inclining during injection. A hook step 34 is provided between the second step 32 and the third step 33 for preventing the needle mount from retracting when a force is exerted on the needle mount during injection. The third step 33 is formed by four annular sector-shaped push blocks 331 arranged with equidistant intervals. The top ends of the annular sector-shaped push blocks 331 are further provided with inner shackles 332'. Fluid pass channels 333 are formed among the annular sector-shaped push blocks 331, and the four inner shackles 332' form a clamping chamber 334. The annular sector-shaped push blocks 331 of the needle mount 3 and the spheroidal push blocks 617 of the automatic retraction means 6 are arranged corresponding to each other and the inner shackles 332' on the annular sector-shaped push blocks 331 and the outer shackles 612' on the spheroidal push blocks 617 form an interference fit with each other. When the outer shackles 612' and the inner shackles 332' are snap-latched to each other, the needle mount 3 can be connected with the automatic retraction means 6. Moreover, a ledge 35 is provided on the inside wall of the needle mount 3 for limiting the position of the needle 4 when being mounted.

Figure 5:
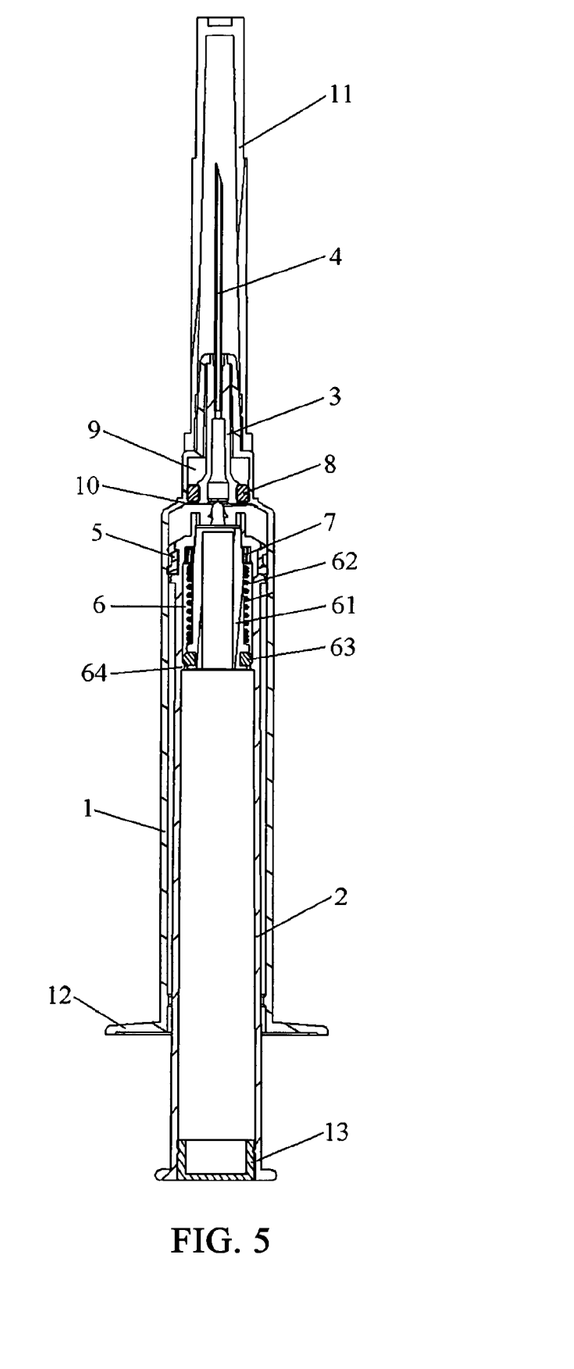
FIG. 5 is a structural scheme of the syringe of a second embodiment of the present invention.

The syringe tube 1 is equipped with a fluid-tight ring 8 fitted on the third step 33 of the needle mount 3 for securing the needle mount 3 and for sealing the gap between the needle mount 3 and the inside wall of the syringe tube 1 so as to prevent fluid leakage. The fluid-tight ring 8 has a same height as that of the third step 33 and has its front end coupled to the hook step 34 provided between the second step 32 and the third step 33 of the needle mount 3 so as to strengthen to the securing of the needle mount 3. A chamber 9 is formed between the front surface of the fluid-tight ring 8 and the inside wall of the syringe tube 1 for accommodating the fluid-tight ring 8 when the fluid-tight ring 8 slides forward and disengages from the needle mount 3. In addition, on the inside wall of the syringe tube 1, a convex retaining ring 10 is further provided at the rear end of the fluid-tight ring 8 for securing the location of the fluid-tight ring 8 and for preventing the needle mount from retracting when a force is exerted on the needle mount during injection. The convex retaining ring 10 and the hook step 34 provided between the second step 32 and the third step 33 of the needle mount 3 cooperate to form a double resistance for effectively preventing the needle mount from retracting when a force is exerted on the needle mount during injection.

Figure 6:
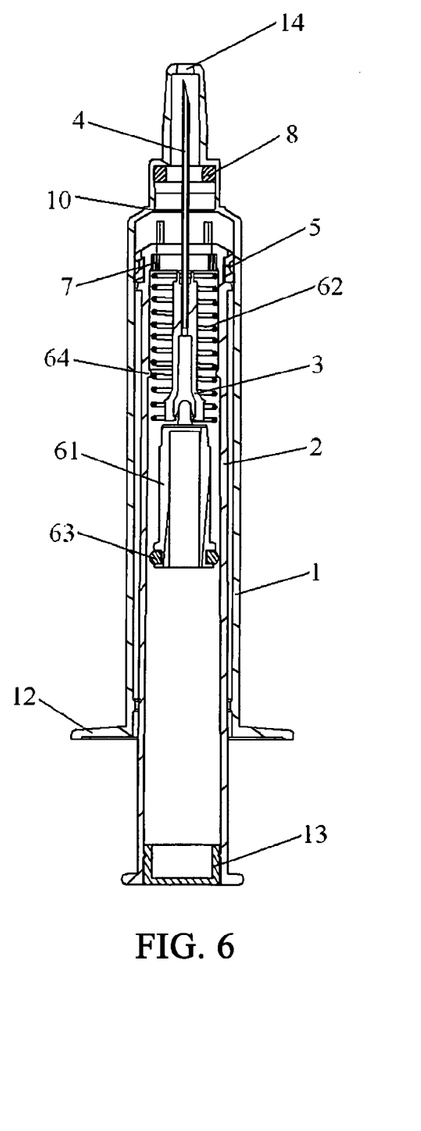
FIG. 6 is a structural scheme of the syringe of the second embodiment of the present invention in which the needle mount and the needle retract into the syringe tube.

During injection, as the push rod 2 is pushed forward, the fluid in the syringe tube 1 flows into the needle 4 through the chamber of the needle mount 3 and is injected into the human body or animal body through the needle 4. When the push rod 2 is pushed to the front end of the syringe tube 1, the spheroidal push blocks 617 on the automatic retraction means 6 enter the clamping chamber 334 in the needle mount 3, and the outer shackles 612' on the spheroidal push blocks 617 and the inner shackles 332' on the annular sector-shaped push blocks 331 are snap-latched to each other under the action of thrust so as to connect the needle mount 3 with the automatic retraction means 6. Meanwhile, the annular sector-shaped push blocks 21 on the push rod 2 are coupled to the rear surface of the fluid-tight ring 8 so that the fluid-tight ring 8 is then pushed forward to slide forward and disengage from the third step 33 of the needle mount 3 and to enter the chamber 9. In the present embodiment, since the snap-latch member is formed by four annular sector-shaped push blocks and spheroidal push blocks arranged with equidistant interval and having shackles, the resistance during the snap-latch is then quartered, and there will be almost no resistance sensed when the push rod is pushed for snap-latch. Moreover, since the fluid pass channels are formed between the annular sector-shaped push blocks on the push rod and the needle mount and the spheroidal push blocks on the automatic retraction means, the fluid remaining in the syringe tube can flow through the fluid pass channels, when the automatic retraction means is engaged with the needle mount, into the chamber of the needle mount 3 and into the needle 4, and therefore, there is no fluid residua in the syringe tube. After the outer shackles 612' and the inner shackles 332' are snap-latched to each other, the push rod 2 is further pushed so that the front end top surface 616 of the retraction rod 61 presses against the terminal end top surface 36 of the needle mount 3, and at this moment the terminal end top surface 36 of the needle mount 3 will exert a counterforce against the front end top surface 616 of the retraction rod 61 forcing the elastic rubber washer 63 of the automatic retraction means 6 to disengage from the position-limiting ring 64, and then the compression spring 62 releases an elastic force to push the retraction rod 61 to retract together with the needle mount 3 and the needle 4 into the syringe tube 1.

The Third Embodiment

As shown in FIG. 10 to FIG. 13, the self-destruction safety syringe according to the present invention comprises a syringe tube 1, a push rod 2, a needle mount 3, a needle 4, a needle cannula 11, a handle 12 and a push plug 13, wherein the needle 4 is mounted on the needle mount 3, the needle mount 3 and the push rod 2 are mounted in the syringe tube 1, and a plunger 5 slidably fitting with the inside wall of the syringe tube 1 is further provided on the front end of the push rod 2.

Figure 10:
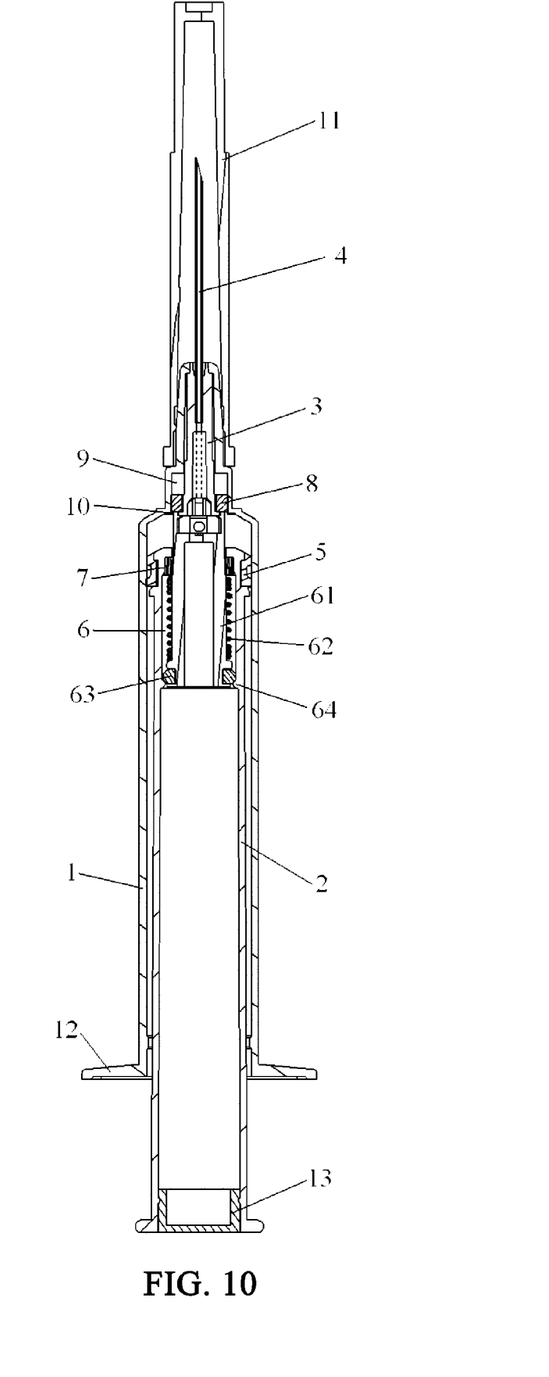
FIG. 10 is a structural scheme of the syringe of a third embodiment of the present invention.
Figure 13:
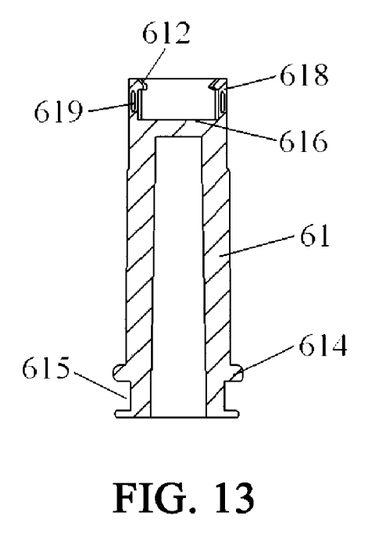
FIG. 13 is a structural scheme of the retraction rod of the third embodiment of the present invention.

An automatic retraction means 6 is mounted in the front end of the chamber of the push rod 2. The automatic retraction means 6 comprises a retraction rod 61, a compression spring 62, an elastic rubber washer 63 and a position-limiting ring 64. A fluid-tight ring 7 is further provided between the front end of the automatic retraction means 6 and the front end of the chamber of the push rod 2. The front end of the automatic retraction means 6 is tightly pressed against the fluid-tight ring 7 so as to seal the gap between the automatic retraction means 6 and the chamber of the push rod 2 to prevent fluid leakage. An annular push block 618 is provided on the circumference of the top end of the retraction rod 61, an inner shackle 612 is provided at the top end of the annular push block 618, and a fluid pass hole 619 is further formed on the wall of the annular push block 618. A ledge 614 is provided on the terminal end of the retraction rod 61, a groove 615 is formed in the middle of the ledge 614, and an elastic rubber washer 63 is placed in the groove 615. A compression spring 62 is fitted around the retraction rod 61 with the front end thereof biased against the terminal end of the fluid-tight ring 7 and the rear end thereof biased against the front surface of the ledge 614 of the retraction rod 61. A position-limiting ring 64 is provided on the inside wall of the push rod 2 to form an interference fit with the elastic rubber washer 63 so as to securely locate the automatic retraction means 6 in the front end of the chamber of the push rod 2.

Figure 12:
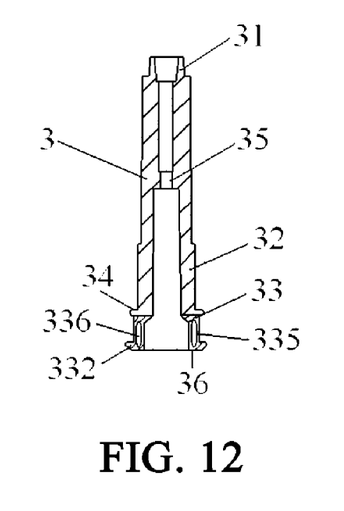
FIG. 12 is a structural scheme of the needle mount of the third embodiment of the present invention.

The needle mount 3 is provided with a first step 31, a second step 32 and a third step 33. The first step 31 slidably fits with the tube hole 14 in the center of the top end of the syringe tube 1 for preventing the needle from inclining during injection. A hook step 34 is provided between the second step 32 and the third step 33 to prevent the needle mount from retracting when a force is exerted on the needle mount during injection. The third step 33 is formed by an annular push block 335, the top end of the annular push block 335 is provided with an outer shackle 332, and a fluid pass hole 336 is further formed on the wall of the annular push block 335. The outer shackle 332 on the annular push block 335 and the inner shackle 612 on the annular push block 618 form an interference fit with each other. When the inner shackle 612 and the outer shackle 332 are snap-latched to each other, the needle mount 3 can be connected with the automatic retraction means 6. Moreover, a ledge 35 is provided on the inside wall of the needle mount 3 for limiting the position of the needle 4 when being mounted.

The syringe tube 1 is equipped with a fluid-tight ring 8 fitted on the third step 33 of the needle mount 3 for securing the needle mount 3 and for sealing the gap between the needle mount 3 and the inside wall of the syringe tube 1 to prevent fluid leakage. The fluid-tight ring 8 has a same height as that of the third step 33 and has its front end coupled to the hook step 34 provided between the second step 32 and the third step 33 of the needle mount 3 so as to strengthen the securing of the needle mount 3. A chamber 9 is further formed between the front surface of the fluid-tight ring 8 and the inside wall of the syringe tube 1 for accommodating the fluid-tight ring 8 when the fluid-tight ring 8 slides forward and disengages from the needle mount 3. In addition, a convex retaining ring 10 is provided on the inside wall of the syringe tube 1 at the rear end of the fluid-tight ring 8 for securing the location of the fluid-tight ring 8 and for preventing the needle mount from retracting when a force is exerted on the needle mount during injection. The convex retaining ring 10 and the hook step 34 provided between the second step 32 and the third step 33 of the needle mount 3 cooperate to form a double resistance for effectively preventing the needle mount from retracting when a force is exerted on the needle mount during injection.

Figure 11:
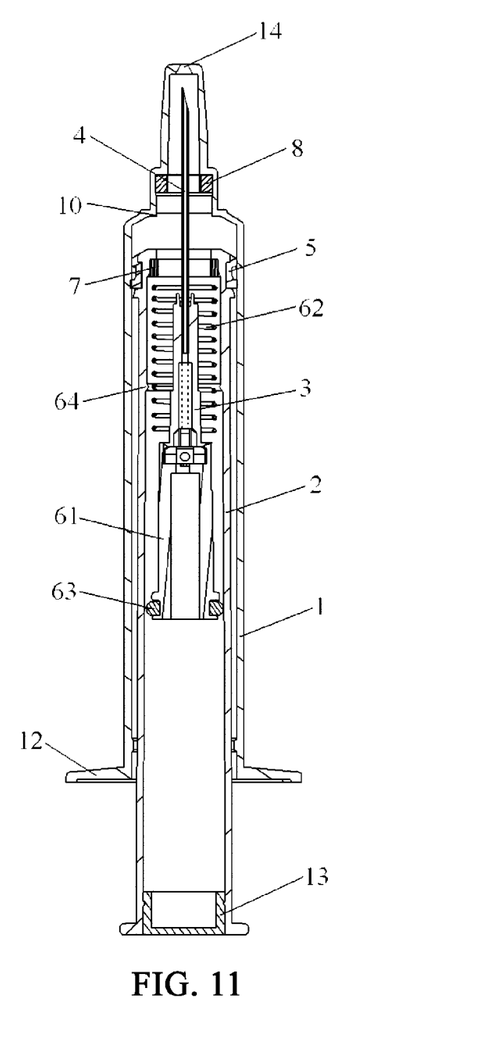
FIG. 11 is a structural scheme of the syringe of the third embodiment of the present invention in which the needle mount and the needle retracts into the syringe tube.

During injection, as the push rod 2 is pushed forward, the fluid in the syringe tube 1 flows into the needle 4 through the chamber of the needle mount 3 and is injected into the human body or animal body through the needle 4. When the push rod 2 is pushed to the front end of the syringe tube 1 and the annular push block 618 on the automatic retraction means 6 is coupled to the annular push block 335 on the needle mount 3, the inner shackle 612 on the annular push block 618 and the outer shackle 332 on the annular push block 335 are snap-latched to each other under the action of thrust so as to connect the needle mount 3 with the automatic retraction means 6. Meanwhile, the annular push block 618 is coupled to the rear surface of the fluid-tight ring 8 so that the fluid-tight ring 8 is then pushed forward to slide forward and disengage from the third step 33 of the needle mount 3 and to enter the chamber 9. In the present embodiment, since fluid pass holes are formed on the wall of the annular push blocks, the fluid remaining in the syringe tube can flow through the fluid pass holes, when the automatic retraction means is coupled to and engaged with the needle mount, into the chamber of the needle mount 3 and into the needle 4, and therefore there is no fluid residua in the syringe tube. After the inner shackle 612 and the outer shackle 332 are snap-latched to each other, the push rod 2 is further pushed so that the front end top surface 616 of the retraction rod 61 presses against the terminal end top surface 36 of the needle mount 3, and at this moment the terminal end top surface 36 of the needle mount 3 will exert a counterforce to the front end top surface 616 of the retraction rod 61 forcing the elastic rubber washer 63 of the automatic retraction means 6 to disengage from the position-limiting ring 64, and then, the compression spring 62 releases an elastic force to push the retraction rod 61 to retract together with the needle mount 3 and the needle 4 into the syringe tube 1.

The Fourth Embodiment

As shown in FIG. 14 to FIG. 18, the self-destruction safety syringe according to the present invention comprises a syringe tube 1, a push rod 2, a needle mount 3, a needle 4, a needle cannula 11, a handle 12 and a push plug 13, wherein the needle 4 is mounted on the needle mount 3, the needle mount 3 and the push rod 2 are mounted in the syringe tube 1, and a plunger 5 slidably fitting with the inside wall of the syringe tube 1 is further provided on the front end of the push rod 2.

An automatic retraction means 6 is mounted in the front end of the chamber of the push rod 2. The automatic retraction means 6 comprises a retraction rod 61, a compression spring 62, an elastic rubber washer 63 and a position-limiting ring 64. A fluid-tight ring 7 is further provided between the front end of the automatic retraction means 6 and the front end of the chamber of the push rod 2. The front end of the automatic retraction means 6 is tightly pressed against the fluid-tight ring 7 so as to seal the gap between the automatic retraction means 6 and the chamber of the push rod 2 to prevent fluid leakage. Four spheroidal push blocks 617 arranged with equidistant intervals are provided on the top center of the retraction rod 61. An outer shackle 612' is further provided on The center of the throat of each spheroidal push block 617. Fluid pass channels 613' are formed among the spheroidal push blocks 617. A ledge 614 is provided on the terminal end of the retraction rod 61, and a groove 615 is formed in the middle of the ledge 614, and the elastic rubber washer 63 is placed in the groove 615. The compression spring 62 is fitted around the retraction rod 61 with the front end thereof biased against the terminal end of the fluid-tight ring 7 and the rear end thereof biased against the front surface of the ledge 614 of the retraction rod 61. The position-limiting ring 64 is provided on the inside wall of the push rod 2 to form an interfere fit with the elastic rubber washer 63 so as to secure the automatic retraction means 6 in the front end of the chamber of the push rod 2. In addition, an annular push block 23 is provided on the circumference of the top end of the push rod 2, and a fluid pass hole 24 is further formed on the wall of the annular push block 23.

Figure 16:
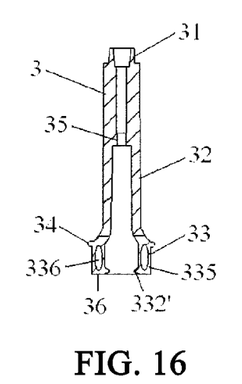
FIG. 16 is a structural scheme of the needle mount of the fourth embodiment of the present invention.
Figure 16A:
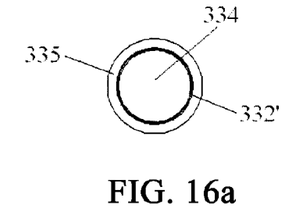
FIG. 16a is a bottom view of FIG. 16.
Figure 17:
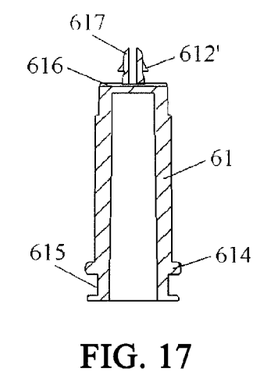
FIG. 17 is a structural scheme of the retraction rod of the fourth embodiment of the present invention.
Figure 17A:
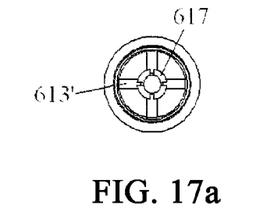
FIG. 17a is a top view of FIG. 17.
Figure 18:
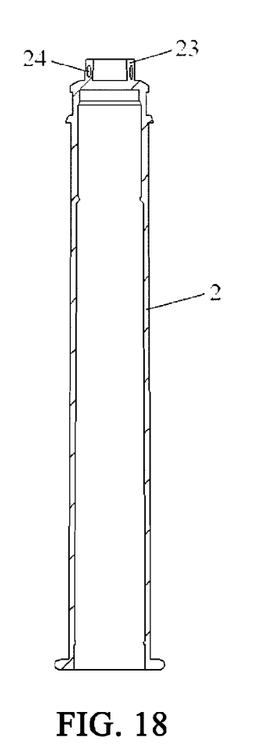
FIG. 18 is a structural scheme of the push rod of the fourth embodiment of the present invention.

The needle mount 3 is provided with a first step 31, a second step 32 and a third step 33. The first step 31 slidably fits with the tube hole 14 in the center of the top end of the syringe tube 1 for preventing the needle from inclining during injection. A hook step 34 is provided between the second step 32 and the third step 33 to prevent the needle mount from retracting when a force is exerted on the needle mount during injection. The third step 33 is formed by an annular push block 335, an inner shackle 332' is provided at the top end of the annular push block 335, a fluid pass hole 336 is further formed on the wall of the annular push block 335, and a clamping chamber 334 is formed by the inner shackle 32. The fluid pass hole 336 on the annular push block 335 and the fluid pass channels 613' among the spheroidal push blocks 617 are arranged corresponding to each other and the inner shackle 332' on the annular push block 335 and the outer shackles 612' on the spheroidal push blocks 617 form an interference fit with each other. When the outer shackles 612' and the inner shackle 332' are snap-latched with each other, the needle mount 3 can be connected with the automatic retraction means 6. Moreover, a ledge 35 is provided on the inside wall of the needle mount 3 for limiting the position of the needle mount 3 when being mounted.

Figure 14:
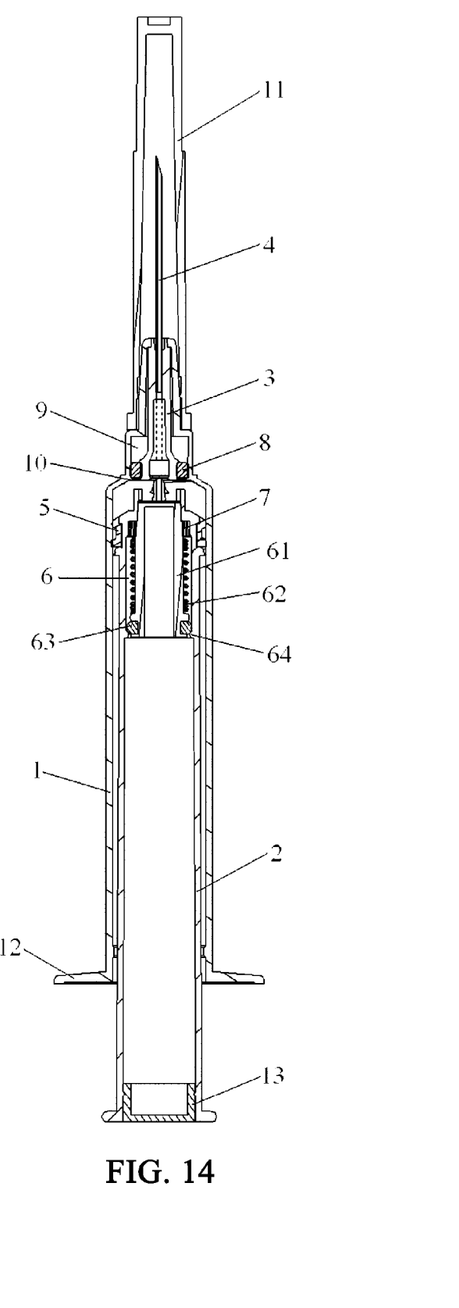
FIG. 14 is a structural scheme of the syringe of a fourth embodiment of the present invention.

The syringe tube 1 is equipped with a fluid-tight ring 8 fitted on the third step 33 of the needle mount 3 for securing the needle mount 3 and for sealing the gap between the needle mount 3 and the inside wall of the syringe tube 1 to prevent fluid leakage. The fluid-tight ring 8 has a same height as that of the third step 33 and has its front end coupled to the hook step 34 provided between the second step 32 and the third step 33 of the needle mount 3 so as to strengthen the securing of the needle mount 3. A chamber 9 is formed between the front surface of the fluid-tight ring 8 and the inside wall of the syringe tube 1 for accommodating the fluid-tight ring 8 when the fluid-tight ring 8 slide forward and disengage from the needle mount 3. In addition, a convex retaining ring 10 is further provided on the inside wall of the syringe tube 1 at the rear end of the fluid-tight ring 8 for securing the location of the fluid-tight ring 8 and for preventing the needle mount retracting when a force is exerted on the needle mount during injection. The convex retaining ring 10 and the hook step 34 provided between the second step 32 and the third step 33 of the needle mount 3 cooperate to form a double resistance for effectively preventing the needle mount from retracting when a force is exerted on the needle mount during injection.

Figure 15:
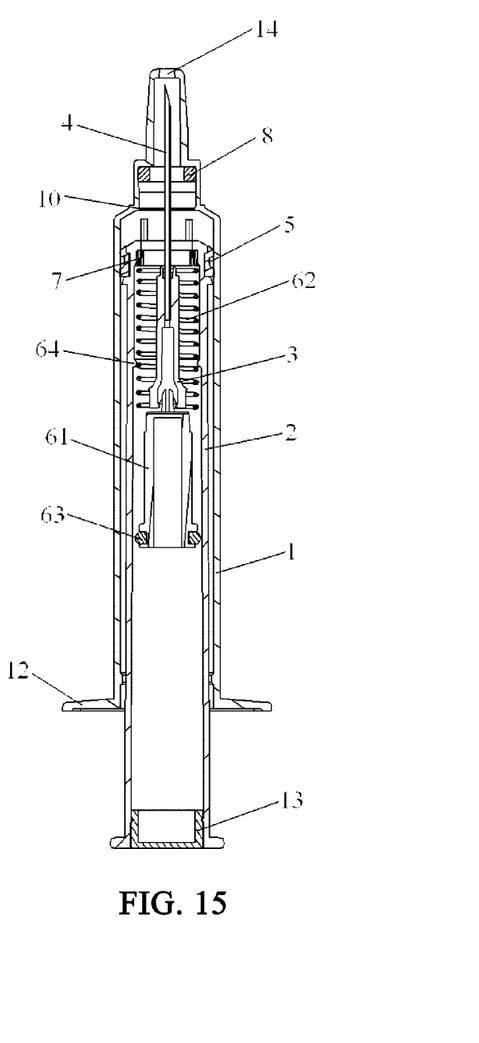
FIG. 15 is a structural scheme of the syringe of the fourth embodiment of the present invention in which the needle mount and the needle retract into the syringe tube.

During injection, as the push rod 2 is pushed forward, the fluid in the syringe tube 1 flows into the needle 4 through the chamber of the needle mount 3 and is injected into the human body or animal body through the needle 4. When the push rod 2 is pushed to the front end of the syringe tube 1, the spheroidal push blocks 617 on the automatic retraction means 6 enter into the clamping chamber 334 in the needle mount 3, and the outer shackles 612' on the spheroidal push blocks 617 and the inner shackle 332' on the annular push block 335 are snap-latched to each other under the action of thrust so as to connect the needle mount 3 with the automatic retraction means 6. Meanwhile, the annular push block 23 on the push rod 2 is coupled to the rear surface of the fluid-tight ring 8 so that the fluid-tight ring 8 is pushed forward to slide forward and disengage from the third step 33 of the needle mount 3 and to enter the chamber 9. In the present embodiment, since the fluid pass holes are formed on the wall of the annular push blocks of the push rod and on the wall of the annular push blocks on the needle mount, and fluid pass channels are formed among the spheroidal push blocks on the automatic retraction means, the fluid remaining in the syringe tube can flow through the fluid pass holes and the fluid pass channels, when the automatic retraction means is engaged with the needle mount, into the chamber of the needle mount 3 and into the needle 4, and therefore there is no fluid residua in the syringe tube. After the outer shackles 612' and the inner shackle 332' are snap-latched to each other, the push rod 2 is further pushed so that the front end top surface 616 of the retraction rod 61 presses against the terminal end top surface 36 of the needle mount 3, and at this moment the terminal end top surface 36 of the needle mount 3 will exert a counterforce to the front end top surface 616 of the retraction rod 61 forcing the elastic rubber washer 63 of the automatic retraction means 6 to disengage from the position-limiting ring 64, and then the compressive spring 62 releases an elastic force to push the retraction rod 61 to retract together with the needle mount 3 and the needle 4 into the syringe tube 1.

The present invention includes but not limits to the contents in the above embodiments. All the other structures having substantively the same content as that in the technical solutions of the present invention should fall into the protection scope of the present invention.

What is claimed is:

1. A disposable self-destruction safety syringe without fluid residua, comprising a syringe tube, a push rod, a needle mount and a needle, wherein the needle is mounted on the needle mount and in fluid communication with a chamber of the needle mount, the needle mount and the push rod are mounted in the syringe tube, and a plunger slidably fitting with an inside wall of the syringe tube is further provided on a front end of the push rod, wherein an automatic retraction means is mounted at a front end of a chamber of the push rod, the automatic retraction means comprises a retraction rod, a compression spring fit around the retraction rod, an elastic rubber washer mounted on a terminal end of the retraction rod and a position-limiting ring provided on an inside wall of the push rod, wherein the elastic rubber washer is engaged with the position-limiting ring so as to form an interference fit with each other to securely locate the automatic retraction means at the front end of the chamber of the push rod, and the retraction rod of the automatic retraction means and the needle mount are each provided with a respective snap-latch member, the two snap-latch members are engaged with each other so as to form an interference fit for connecting the needle mount with the automatic retraction means, wherein each of the snap-latch members is provided with a fluid pass channel, the fluid pass channels are formed to be in fluid communication with the chamber of the syringe tube and the needle mount when the two snap-latch members engage with each other to form interference fit so that fluid remaining inside the syringe tube flows through the fluid pass channels into the chamber of the needle mount and into the needle, so as to be injected into the human body.

2. The self-destruction safety syringe according to claim 1, wherein a first fluid tight ring is further provided between the automatic retraction means and the front end of the chamber of the push rod for sealing a gap between the automatic retraction means and the chamber of the push rod so as to prevent fluid leakage.

3. The self-destruction safety syringe according to claim 2, wherein each of the plunger, the elastic rubber washer and the first fluid-tight ring comprise synthetic rubber materials.

4. The self-destruction safety syringe according to claim 1, wherein the needle mount is provided with a first step, a second step and a third step, wherein the first step fits with a tube hole in a top end of the syringe tube, so as to prevent the needle from inclining during injection a hook step is provided at between the second step and the third step so as to prevent the needle mount from retraction when a force is exerted on the needle mount during injection and the snap-latch member of the needle mount is provided on the third step.

5. The self-destruction safety syringe according to claim 4, wherein an inside wall of the needle mount is further provided with a ledge for limiting the position of the needle being mounted.

6. The self-destruction safety syringe according to claim 1, wherein the syringe tube is provided inside with a second fluid-tight ring fitted around the needle mount for securing the needle mount and for sealing a gap between the needle mount and the inside wall of the syringe tube so as to prevent fluid leakage.

7. The self-destruction safety syringe according to claim 6, wherein a chamber is formed between a front surface of the second fluid-tight ring and the inside wall of the syringe tube for accommodating the second fluid-tight ring when the second fluid-tight ring slides forward to disengage from the needle mount.

8. The self-destruction safety syringe according to claim 7, wherein an annular push block is provided on the circumference of a top end of the push rod for pushing the second fluid-tight ring to slide forward to disengage from the needle mount and the annular push block is provided with a fluid pass channel such that the fluid remaining inside the syringe tube flows through the fluid pass channel, when the annular push block is engaged with the second fluid-tight ring, into the chamber of the needle mount and into the needle.

9. The self-destruction safety syringe according to claim 6, wherein a convex retaining ring is provided on the inside wall of the syringe tube at a rear end of the second fluid-tight ring so as to prevent the needle mount from retraction when a force is exerted on the needle mount during injection.

10. The self-destruction safety syringe according to claim 6, wherein each of the plunger, the elastic rubber washer and the second fluid-tight ring comprise synthetic rubber materials.

11. The self-destruction safety syringe according to claim 1, wherein each of the plunger and the elastic rubber washer comprise synthetic rubber materials.

12. The self-destruction safety syringe according to claim 1, further comprising a needle cannula fit on a front end of the syringe tube and a push plug provided at a terminal end of the push rod.

\* \* \* \* \*